United States Patent

Kopsala

[11] Patent Number: 5,732,119
[45] Date of Patent: Mar. 24, 1998

[54] METHOD FOR THE AUTOMATIC ADJUSTMENT OF EXPOSURE PARAMETERS IN AN IMAGING APPARATUS OPERATING ON LINEAR TOMOGRAPHIC PRINCIPLES

[75] Inventor: Panu Kopsala, Tuusula, Finland

[73] Assignee: Instrumentarium Corporation, Helsinki, Finland

[21] Appl. No.: 646,615

[22] Filed: May 8, 1996

[30] Foreign Application Priority Data

May 12, 1995 [FI] Finland .................................. 952313

[51] Int. Cl.⁶ .................................................. A61B 6/14
[52] U.S. Cl. ...................... 378/26; 378/38; 378/39
[58] Field of Search .......................... 378/38, 39, 40, 378/21, 25, 168, 26

[56] References Cited

U.S. PATENT DOCUMENTS

| | | |
|---|---|---|
| 4,618,974 | 10/1986 | Grassme et al. . |
| 4,783,793 | 11/1988 | Virta et al. . |
| 4,813,060 | 3/1989 | Heubeck et al. . |
| 4,815,115 | 3/1989 | Nieminen et al. . |
| 5,033,070 | 7/1991 | Kanerva .................... 378/40 X |
| 5,195,114 | 3/1993 | Sairenji et al. ............ 373/40 |
| 5,214,686 | 5/1993 | Webber ...................... 378/40 X |
| 5,386,448 | 1/1995 | Tammisalo et al. . |
| 5,425,065 | 6/1995 | Järvenin . |
| 5,444,754 | 8/1995 | Wederhorn et al. ........ 378/38 |

FOREIGN PATENT DOCUMENTS

| | | |
|---|---|---|
| 512964 | 11/1992 | European Pat. Off. . |
| 90618 | 11/1993 | Finland . |
| 922733 | 2/1994 | Finland . |

*Primary Examiner*—David P. Porta
*Attorney, Agent, or Firm*—Andrus, Sceales, Starke & Sawall

[57] ABSTRACT

The invention relates to a method for the automatic adjustment of exposure parameters in an imaging apparatus operating on linear tomographic principles and intended for the slice imaging of the region of denture and temporomandibular joints. The method includes a stage for measuring a radiation (8) transmitted through the skull and for adjusting exposure parameters on the basis of the measuring result. According to the invention, a first imaging sequence, at the start of which the exposure parameters are adjusted, is commenced from such a direction (11a, 11b) that the passage of radiation is secured through thick skull portions and that a subsequent imaging sequence in a direction (12–17) other than the previous direction is carried out by varying the exposure parameters programmatically by a predetermined deviation or by effecting the automatic adjustment of exposure parameters on the basis of new measuring results, whose starting parameters have been obtained by varying the exposure parameters programmatically by a predetermined deviation.

15 Claims, 3 Drawing Sheets

1

METHOD FOR THE AUTOMATIC ADJUSTMENT OF EXPOSURE PARAMETERS IN AN IMAGING APPARATUS OPERATING ON LINEAR TOMOGRAPHIC PRINCIPLES

BACKGROUND OF THE INVENTION

The present invention relates to a method for the automatic adjustment of exposure parameters in an imaging apparatus operating on linear tomographic principles and intended for the slice imaging of the region of denture and temporomandibular joints, said method including a stage for measuring a radiation transmitted through the skull and for adjusting exposure parameters (kV, mA and/or exposure time) on the basis of the measuring result.

When taking slice images, the direction of radiation is often such that at least some of the radiation in at least some stage of rotary movement travels along the outer side of the dental arch without transmitting at all through thick skull portions, e.g. bones in the back of the skull or bones of the dental arch. Thus, it has been considered impossible to accomplish reliable automatic adjustment of exposure parameters for linear tomographic imaging.

SUMMARY OF THE INVENTION

Hence, the most important object of the invention is to provide a method for the automatic adjustment of exposure parameters in an imaging apparatus operating on linear tomographic principles and, in order to fulfil this object, a method according to a first aspect of the invention is characterized in that a first imaging sequence, at the start of which the exposure parameters are adjusted, is commenced from such a direction that the passage of radiation is secured through thick skull portions and that a subsequent imaging sequence in a direction other than the previous direction is carried out by varying the exposure parameters programmatically by a predetermined deviation. A method according to a second aspect of the invention is characterized in that a first imaging sequence, at the start of which the exposure parameters are adjusted, is commenced from such a direction that the passage of radiation is secured through thick skull portions and that a subsequent imaging sequence in a direction other than the previous direction is carried out by effecting the automatic adjustment of exposure parameters on the basis of new measuring results, whose starting parameters have been obtained by varying the exposure parameters programmatically by a predetermined deviation.

BRIEF DESCRIPTION OF THE INVENTION

The invention will now be described in more detail with reference made to the accompanying drawings, in which.

DETAILED DESCRIPTION OF THE PREFERRED EMBODIMENT

Figure 1:
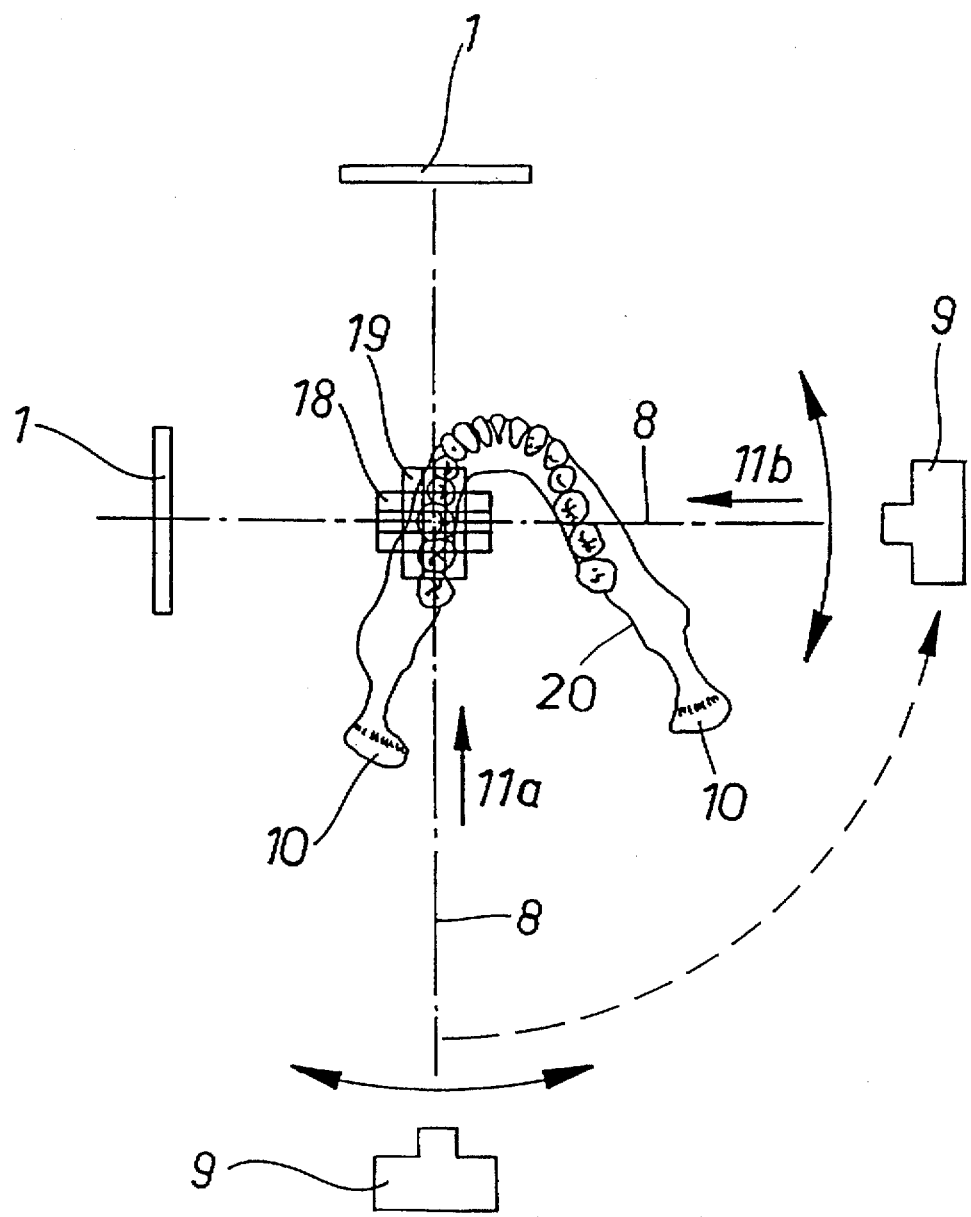
FIG. 1 shows schematically one way of carrying out the method.
Figure 2:
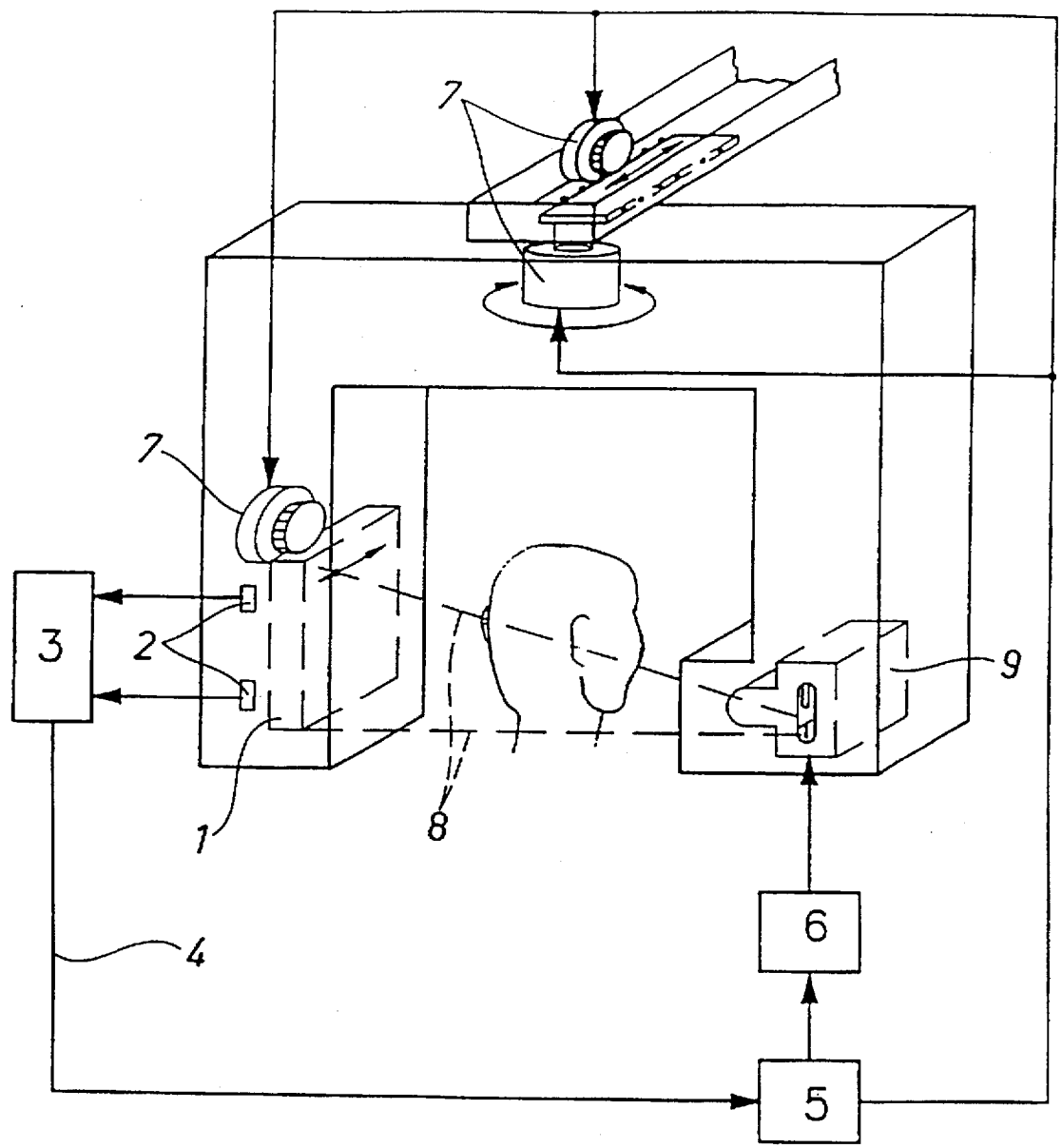
FIG. 2 shows one assembly of equipment for carrying out the invention.

FIG. 1 shows by way of example the imaging of cross-sectional and longitudinal slices 18 and 19, respectively. The imaging sequence is commenced from a direction 11$a$ between temporomandibular joints 10, whereby a beam of rays 8 emitting from an X-ray tube definitely transmits through the posterior bones of the skull (not shown) as well as part of a dental arch 20. At the start of an imaging sequence session the apparatus is set up with certain hypothetical imaging parameters. As shown in FIGS. 1 and 2, the beam of rays 8 progresses to a film contained in a cassette 1 and further to one or more detectors 2, possibly e.g. photodiodes, arranged behind the cassette 1. A signal from the detector 2 is amplified with an amplifier 3 and carried to a control unit 5 for determining required imaging parameters with the help of measuring results by correcting the hypothetical parameters, if necessary. When imaging in a direction other than this starting direction, e.g. longitudinal slices in a direction 11$b$, the control unit 5 adjusts exposure parameters such that the reference parameters of tube voltage and/or tube current of the X-ray tube are changed by means of a differential amplifier included in the regulating circuit of an X-ray generator 6 and/or the speeds of imaging movements are compensated for accordingly by changing the setup value of imaging movements control elements, e.g. the operating frequency of stepping motors 7.

Figure 3:
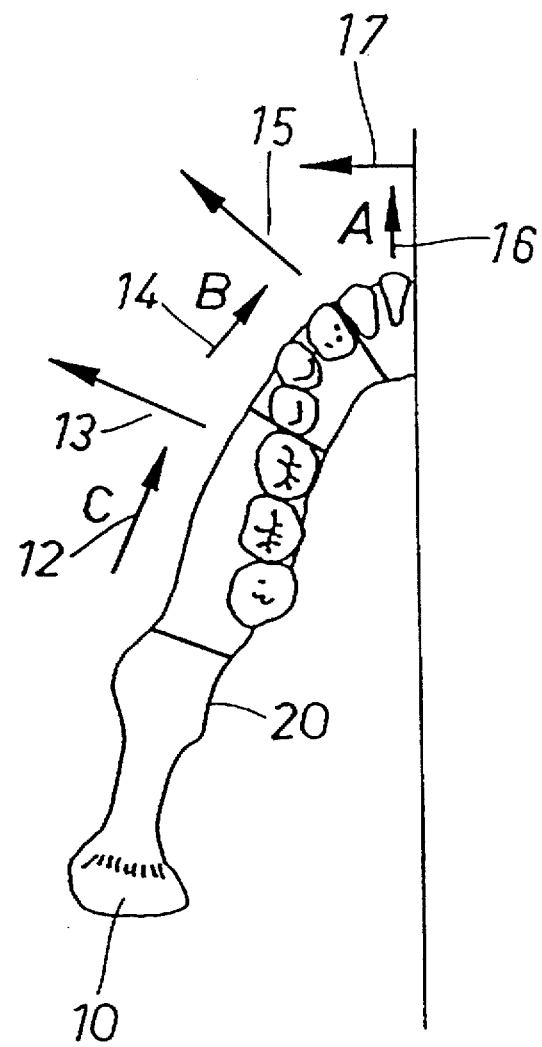
FIG. 3 shows schematically the division of a dental arch in different imaging areas which are provided with different amplification factors for the variation of imaging parameters to comply with a given imaging area and imaging direction.

The variation increments of imaging parameters are given predetermined exposure-value compensating factors for various dental-arch imaging areas and/or directions. These compensating factors are necessary in an effort to achieve equal film density regarding slices extending in various directions and/or located in various areas. The compensating factors are selected such that the factor of +1 results in an exposure parameter which is 25% more than the exposure parameter of an image being compared, i.e. the compensating factor can be presented as $1,25^n$, wherein the power n is an integer. FIG. 3 illustrates schematically the division of a dental half-arch in various imaging areas A, B and C, wherein the various directions (arrows 12–17) can be experimentally provided with necessary compensating factors for exposure parameters. In area B, for example, the factor in direction 15 can be +1 and in direction 14 +5 and, thus, taking an image in direction 15 produces on the film a certain darkening and, with respect to this darkening, the factor of an image taken in direction 14 is $1,25^5/1,25^1=1,25^4$ times higher.

A method according to a second aspect of the invention involves new measurements, whose starting parameters have been obtained by varying the exposure parameters programmatically by a predetermined deviation.

I claim:

1. A method for automatically adjusting exposure parameters in an imaging apparatus operating on linear tomographic principles to provide tomographic imaging of the region of the teeth and temporomandibular joints of the skull, said method comprising the steps of:

carrying out a first imaging sequence comprising the steps of:

establishing initial exposure parameters;

passing radiation in a first direction such that the radiation will pass through portions of the skull having at least a predetermined thickness;

measuring the radiation passed through the skull; and adjusting the initial exposure parameters on the basis of the measuring result; and carrying out a second imaging sequence comprising the steps of:

altering the adjusted exposure parameters programmatically by a predetermined deviation;

passing radiation through the teeth and temporomandibular joint region, and when passing radiation in a direction different than the first direction, using the altered exposure parameters; and obtaining a tomographic image from the radiation passed through the teeth and temporomandibular joint region.

2. A method as set forth in claim 1, characterized in that various imaging areas (A, B, C) and directions (11a, 11b; 12-17) in the region of the teeth and temporomandibular joints are given predetermined exposure-value compensating factors, according to which the adjusted exposure parameters of the first imaging sequence are altered when passing radiation extending in each imaging area.

3. A method as set forth in claim 1, characterized in that the first imaging sequence is commenced from the direction (11a), wherein the radiation (8) passes between temporomandibular joints (10).

4. A method as set forth in claim 2 wherein the region of the teeth and temporomandibular joints has a dental arch (20) and wherein the method is characterized in that the first imaging sequence is commenced from a first direction (11b) along which the radiation (8) passes twice through a dental arch (20).

5. A method as set forth in claim 2, wherein the imaging apparatus has rotatable imaging elements and wherein the method is characterized in that a compensation required by the adjustment and alteration of exposure parameters is effected by varying the rotating speed of imaging elements.

6. A method as set forth in claim 2, characterized in that the first imaging sequence is commenced from a direction (11a), wherein the radiation (8) passes between temporomandibular joints (10).

7. A method as set forth in claim 6, wherein the imaging apparatus has rotatable imaging elements and wherein the method is characterized in that a compensation required by the adjustment and alteration of exposure parameters is effected by varying the rotating speed of imaging elements.

8. A method as set forth in claim 1, wherein the region of the teeth and temporomandibular joints has a dental arch (20) and wherein the method is characterized in that the first imaging sequence is commenced from a first direction (11b) along which the radiation (8) passes twice through a dental arch (20).

9. A method as set forth in claim 8, wherein the imaging apparatus has rotatable imaging elements and wherein the method is characterized in that a compensation required by the adjustment and alteration of exposure parameters is effected by varying the rotating speed of imaging elements.

10. A method as set forth in claim 1 wherein the imaging apparatus has rotatable imaging elements and wherein the method is characterized in that a compensation required by the adjustment and alteration of exposure parameters is effected by varying the rotating speed of imaging elements.

11. A method for automatically adjusting exposure parameters in an imaging apparatus operating on linear tomographic principles to provide tomographic imaging of the region of the teeth and temporomandibular joints of the skull, said method comprising the steps of:

carrying out a first imaging sequence comprising the steps of:

establishing initial exposure parameters;

passing radiation in a first direction such that the radiation will pass through portions of the skull having at least a predetermined thickness;

measuring the radiation passed through the skull; and adjusting the initial exposure parameters on the basis of the measuring result; and carrying out a second imaging sequence comprising the steps of:

altering the adjusted exposure parameters programmatically by a predetermined deviation;

passing radiation through the teeth and temporomandibular joint region, and when passing radiation in a direction different than the first direction, using the altered exposure parameters;

measuring the radiation passed through the teeth and temporomandibular joint region;

adjusting the altered exposure parameters on the basis of the measuring result;

passing radiation through the teeth and temporomandibular region area using the adjusted, altered parameters; and obtaining an image from the radiation passed through the teeth and temporomandibular joint region.

12. A method as set forth in claim 11, characterized in that various imaging areas (A, B, C) and directions (11a, 11b; 12-17) in the region of the teeth and temporomandibular joints are given predetermined exposure-value compensating factors, according to which the adjusted exposure parameters of the first imaging sequence are altered when passing radiation extending in each imaging area.

13. A method as set forth in claim 11, characterized in that the first imaging sequence is commenced from the direction (11a), wherein the radiation (8) passes between temporomandibular joints (10).

14. A method as set forth in claim 11, wherein the region of the teeth and temporomandibular joints has a dental arch (20) and wherein the method is characterized in that the first imaging sequence is commenced from a first direction (11b) along which the radiation (8) passes twice through a dental arch (20).

15. A method as set forth in claim 11, wherein the imaging apparatus has rotatable imaging elements and wherein the method is characterized in that a compensation required by the adjustment and alteration of exposure parameters is effected by varying the rotating speed of imaging elements.

* * * * *

UNITED STATES PATENT AND TRADEMARK OFFICE
CERTIFICATE OF CORRECTION

PATENT NO: 5,732,119

DATED: March 24, 1998

INVENTORS: Panu Kopsala

It is certified that error appears in the above-identified patent and that said Letters Patent is hereby corrected as shown below:

CLAIM 2, Col. 3, Line 11, after "in" insert ---a certain direction and passing through;

Col. 4, Line 35, after "in" insert ---a certain direction and passing through---

Signed and Sealed this

Sixteenth Day of January, 2001

Attest:

Attesting Officer

Q. TODD DICKINSON

Commissioner of Patents and Trademarks